United States Patent [19]

Hsu

[11] Patent Number: 4,816,000

[45] Date of Patent: Mar. 28, 1989

[54] STUFFED TOY WITH ENCLOSED FLUID CONTAINER

[76] Inventor: Tony T. Hsu, 18202 Charter Rd., Villa Park, Calif. 92667

[21] Appl. No.: 25,358

[22] Filed: Mar. 13, 1987

[51] Int. Cl.⁴ .............................................. A63H 3/00
[52] U.S. Cl. ..................................... 446/74; 206/457; 446/371; 383/901
[58] Field of Search ................... 446/74, 268, 369, 73, 446/76, 371, 391; 206/457, 216; 5/441; 215/11.6; 150/52 E

[56] References Cited

U.S. PATENT DOCUMENTS

| | | | |
|---|---|---|---|
| 853,639 | 5/1907 | Hincks | 446/74 X |
| 1,346,176 | 7/1920 | Chambers | 446/74 X |
| 1,758,024 | 5/1930 | Blomquist | 446/74 |
| 2,129,654 | 9/1938 | Dennis | 446/74 X |
| 3,105,612 | 10/1963 | Krasnoff et al. | 446/74 X |
| 4,568,298 | 2/1986 | Acree | 446/74 |
| 4,714,445 | 12/1987 | Templeton | 446/74 |

FOREIGN PATENT DOCUMENTS 997078 12/1951 France ................... 446/74
74794 3/1949 Norway ................... 446/74

Primary Examiner—Mickey Yu
Attorney, Agent, or Firm—Fulwider Patton Rieber Lee & Utecht

[57] ABSTRACT

A stuffed toy animal including an enclosed flexible fluid container and a soft furry exterior having a head portion and a plurality of extremities stuffed with a non-flammable material and a body portion accessible via a zipper for accommodating the flexible fluid container which is secured in place by a plurality of elastic securing straps. The flexible container is filled with a hot fluid if heat is to be radiated or filled with a cold fluid if heat is to be absorbed. The flexible container is then fitted with a leakproof stopper and inserted into the stuffed toy animal beneath the securing straps of the body portion. The stuffed toy animal may now be held by a human or be utilized as a pillow for a small pet for providing a warming or cooling effect.

In a second embodiment, the fluid container is permanently formed within the body portion and access to the container is provided by removing the head portion.

6 Claims, 3 Drawing Sheets

STUFFED TOY WITH ENCLOSED FLUID CONTAINER

BACKGROUND OF THE INVENTION

This invention relates generally to stuffed toys, and more particularly, to a stuffed animal having a flexible fluid container for housing a fluid medium acting as a heat source or a heat sink.

It is common practice in the toy industry to manufacture stuffed toy animals of various sizes and shapes. These stuffed toys are generally directed towards that sector of the market which caters to children. Generally the stuffed animals are cloaked in material which is soft to the touch with the toy animal generally being stuffed with a material which is lightweight and resistant to wear such as a polyester or the like.

The stuffed animals also will often include cosmetic facial features to provide an identity element. Upon applying physical pressure to an air actuated noise device often located within the stuffed animal, an audible sound appears to be uttered providing a perceived personality to the inanimate toy. Other designs may also include a mechanically driven or a spring operated noise generator which when actuated will play theme songs of fairy tales or the like.

Although the stuffed animals are generally marketed to children and adults alike, an alternate sales effort is directed towards the owners of small pets. It is well known that small pets such as dogs and cats enjoy playing with a variety of stuffed animal-type toys. Such toys designed for small pets are often designed for heavy duty use, include a soft exterior cover and a cosmetically recognizable appearance.

The stuffed animals which are currently available for use by humans and pets alike for companionship, are generally at ambient temperature. Thus, if the ambient temperature is cold then the stuffed animal is likely to be at that ambient temperature and will not serve to warm the person or animal that is in contact with the stuffed animal. Further, if the ambient temperature is very warm, the stuffed animal does not serve to cool the person or the animal in contact therewith. Since the stuffed animals are often transported with the children and the pets when travelling away from the home, such as in an automobile or an airplane or train on vacation, those concerned with the design and development of stuffed animals in the toy industry have long recognized the need for an improved stuffed animal having a means for radiating warmth in the cold weather and for absorbing heat in the hot weather. Further, the stuffed animal should be comprised of non-flammable material, should be inexpensive to manufacture, should be an energy efficient heat source and heat sink, and should be conveniently disassembled for washing the outer material. Finally, the stuffed animal should not require a replaceable energy source such as a battery in order to provide the heating and cooling effect. The present invention fulfills all of these needs.

SUMMARY OF THE INVENTION

Briefly, and in general terms, the present invention provides a new and improved stuffed toy having an enclosed fluid container embodying novel methods and apparatus for providing an energy efficient heat source in the cold weather and an energy efficient heat sink in the warm weather.

Basically, the present invention is directed to a stuffed toy animal which includes an enclosed fluid container having a soft furry exterior designed to be held by a human or to act as a pillow for a small animal and which radiates or absorbs heat depending upon the contents of the enclosed container.

In a presently preferred embodiment, by way of example and not necessarily by way of limitation, the present invention may include an outer enclosure shaped like an animal having a head portion, a body portion, a tail and corresponding extremities. The outer enclosure is normally fashioned by stuffing the head portion and extremities with a non-flammable material such as a polyester cotton.

The mid-section of the stuffed toy animal is not stuffed with the non-flammable material and is accessible via a zipper located on the underneath (stomach) portion of the body portion. The interior section of the body portion includes a plurality of elastic-securing straps sewn into the material which act to secure the fluid container when inserted into the stuffed toy. The fluid container may be any flexible fluid enclosure having an opening for inserting and removing a fluid and a stopper device for sealing the opening. The head portion of the stuffed animal may include normal facial features to complete the cosmetic appearance of the animal for identification while the fabric of the outer enclosure may be soft and furry in a short or a long hair version.

In accordance with the invention, the body portion of the stuffed animal is accessed by operating the zipper from the tail to the head exposing the securing straps. Upon removing the stopper, the fluid container is filled with a hot fluid if heat is to be radiated or filled with a cold fluid if heat is to be absorbed. After replacing the stopper, the fluid container is inserted into the body of the stuffed animal with the sealed opening of the fluid container fitting into the lower head portion and the flexible portion of the fluid container fitting beneath the securing straps in the body portion. Once the fluid container is inserted, the zipper is operated from the head to the tail section closing the body portion and hiding the fluid container from view. The stuffed toy animal fitted with the fluid container may now be held by a human or be utilized as a pillow for a small pet for providing a warming or cooling effect.

An alternative embodiment is also disclosed employing a similar stuffed toy animal having a built-in flexible fluid container.

The new and improved stuffed toy animal of the present invention provides an energy efficient heat source and heat sink, is fashioned from a non-flammable material which is safe for use by children and is economical and inexpensive to manufacture. Additionally, the stuffed animal is convenient to disassemble for adding to and removing fluid from the flexible fluid container and the outer enclosure is comprised of material which is washable for keeping the stuffed toy animal in a sanitary condition when subject to wear by children and small pets.

These and other objects and advantages of the invention will become apparent from the following more detailed description when taken in conjunction with the accompanying drawings which illustrate by way of example, the features of the invention.

DESCRIPTION OF THE PREFERRED EMBODIMENT

Figure 1A:
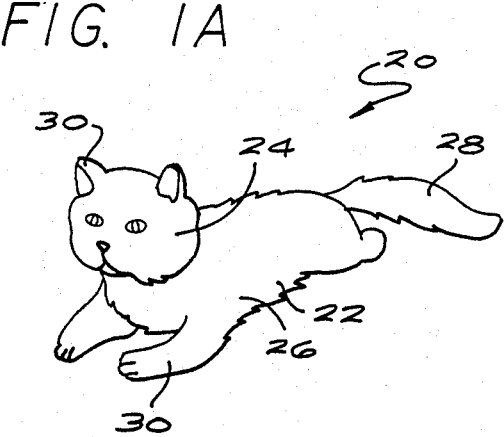
FIGS. 1A and 1B are prospective views of a stuffed toy having an enclosed fluid container in accordance with the present invention.

As shown in the drawings for purposes of illustration, the invention is embodied in a stuffed toy animal with an enclosed fluid container referred to by the general reference numeral 20 and incorporating the present invention. The stuffed toy animal 20 is of the type having an outer enclosure 22 shaped like an animal having a head portion 24, a body portion 26, a tail 28 and a plurality of corresponding extremities 30. The outer enclosure 22 comprises a soft furry exterior while the body portion 26 includes a flexible fluid container 32 for housing of fluid.

In accordance with the present invention, the stuffed toy animal 20 cooperates with the flexible fluid container 32 and the plurality of cosmetic identification features for providing an inanimate toy companion for a human or a small pet capable of heat radiation or absorption as desired. Further, the stuffed toy animal provides an energy efficient heat source and heat sink, is stuffed with and fashioned from a safe non-flammable material and is economical and inexpensive to manufacture. The flexible fluid container 32 is convenient to remove by way of a zipper means 34 for changing the fluid therein, and the outer enclosure is comprised of a material which is washable for keeping the stuffed toy animal in a sanitary condition.

Figure 1B:
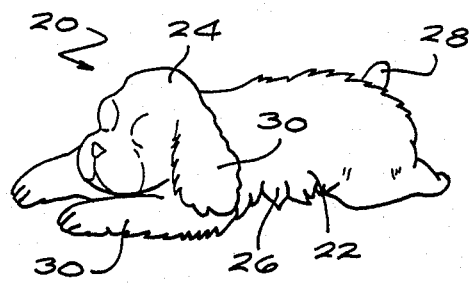

Referring now to the drawings, and particularly to FIGS. 1A and 1B thereof, there is shown the stuffed toy animal 20, the outer enclosure 22, the head portion 24, the body portion 26, the tail 28, and the plurality of corresponding extremities 30. The outer enclosures 22 are shaped like small animals as can be seen from FIGS. 1A and 1B. The head portion 24 is stuffed with a non-flammable material such as a polyester cotton to ensure the safety of small children and to comply with all fire code regulations. The extremities 30 which include the legs and the ears of the stuffed toy animals are also stuffed with the non-flammable polyester material, however, the tail is not.

The outer enclosure 22 is comprised of a fabric which is generally soft and furry on the outside in either a short hair or a long hair version. The interior of the outer enclosure 22 is of a coarse knitted texture which facilitates installing the zipper means 34 by a sewing process within the bottom of the body portion 26 (shown best in FIGS. 5 through 7B). The facial features are comprised of novelty items employed in combination to complete the cosmetic appearance. The eyes, the nose and the mouth design of the stuffed toy animals 20 illustrated in FIGS. 1A and 1B are comprised of elements which are commercially available and old in the art.

Figure 2A:
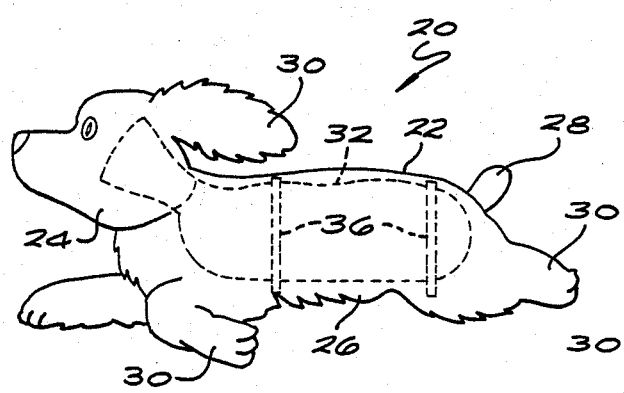
FIGS. 2A and 2B are side elevational views of the stuffed toy of FIGS. 1A and 1B respectively illustrating the fluid container in phantom.
Figure 2B:
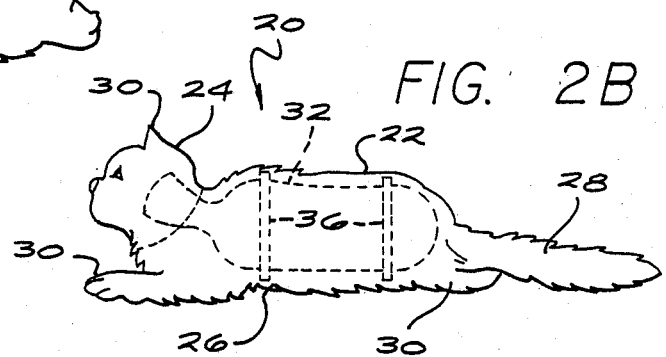
Figure 3:
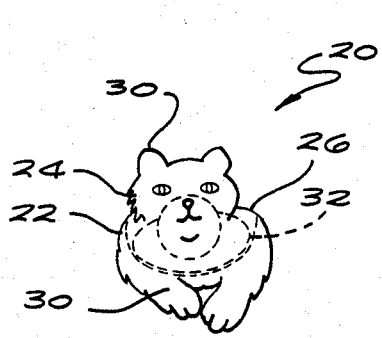
FIG. 3 is a frontal elevational view of the stuffed toy of FIG. 1A illustrating the fluid container in phantoms.
Figure 4:
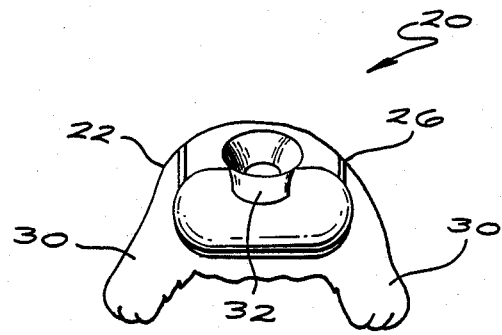
FIG. 4 is a frontal elevational view of the stuffed toy of FIG. 1B with the head portion removed.

A side elevational view of the stuffed toy animals 20 illustrating the flexible fluid container 32 is shown in FIGS. 2A and 2B. The flexible fluid container 32 is shown mounted within the body portion 26 with the mouth of the container 32 extending into the head portion 24 of the stuffed toy animal 20. The mouth of the flexible fluid container 32 is shown in phantom as extending into the head portion 24 of the stuffed toy animal 20 in FIG. 3. If the head portion 24 of the stuffed toy animal 20 is removed, the mouth of the flexible fluid container 32 is visible extending from the body portion 26 as shown in FIG. 4.

The container 32 is retained in position within the body portion 26 by a plurality of elastic securing straps 36 extending across the body portion 26 as illustrated in FIGS. 2A and 2B. The elastic securing straps 36 are comprised of a fire resistant material and are elastic in nature for accommodating the insertion of the flexible fluid container 32 into the body portion 26. Note that for illustrative purposes only, the elastic securing straps are spaced such that at least one securing strap is attached to the inside fabric of the body portion 26 behind the shoulder while another strap is attached in front of the hind quarter of the stuffed toy animal 20.

Figure 5:
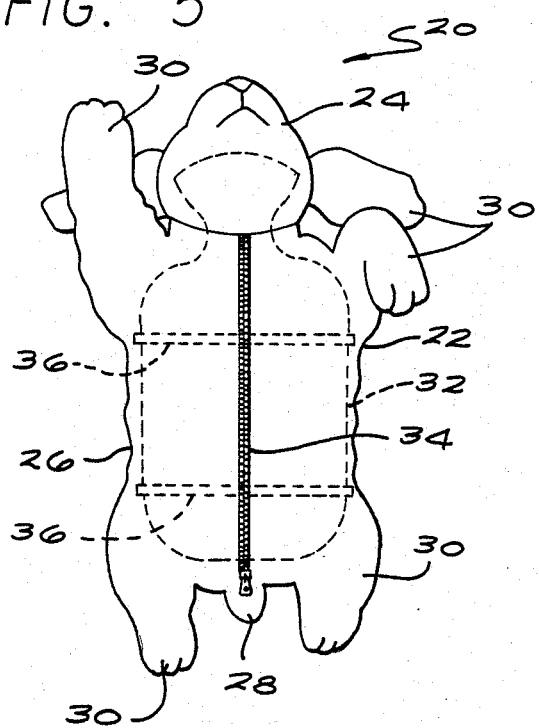
FIG. 5 is a planar view of the bottom portion of the stuffed toy animal of FIG. 1B illustrating the mechanical means for providing access to the body portion.

If the stuffed toy animal 20 is positioned so that the bottom (stomach) portion is exposed, the zipper means 34 providing access to the body portion 26 is accessible. The zipper means may be any commercially available mechanical means for opening and closing the body portion 26 by operation of a handle for manipulating the teeth of the zipper means as shown in FIG. 5. The zipper means 34 may be the usual metal zipper or may be comprised of a lightweight material such as nylon or even strips of Velcro locking material. The elastic securing straps 36 are shown in phantom supporting the fluid container 32 beneath the outer enclosure 22 in FIG. 5.

Figure 6:
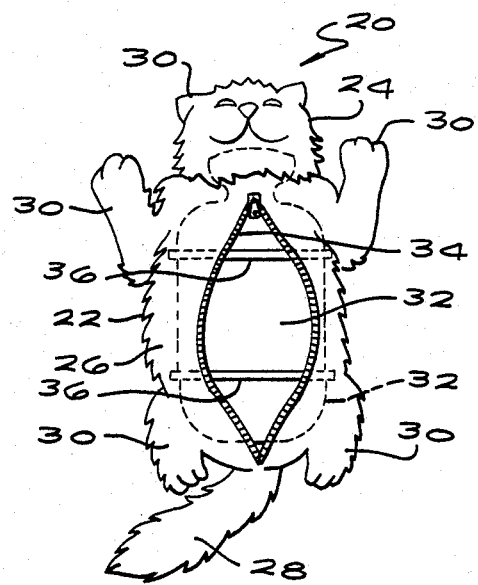
FIG. 6 is a planar view of the bottom portion of the stuffed toy animal of FIG. 1A illustrating the mechanical means for exposing the fluid container.

If, for illustrative purposes only and not by way of limitation, the zipper means 34 is manually operated from the tail 28 to the head portion 24, the outer enclosure 22 is separated and the container 32 is visible as shown in FIG. 6. The container 32 is shown in phantom as completely filling the body portion 26 of the stuffed toy animal 20 with the mouth of the container 32 extending into the head portion 24. The fluid container 32 may be any commercially available fluid enclosure which is flexible in nature and is capable of retaining both hot and cold fluids. The container 32 must include a mouth or opening which is sealed by a stopper for preventing leakage of the fluid.

Also, the container must be fabricated from a material having a temperature coefficient which is adequate to transmit heat when the container is filled with a hot fluid and capable of absorbing heat when the container is filled with a cold fluid. An example of the container 32 is a flexible water bottle having a mouth portion sufficiently large to accept standard size ice cubes as well as hot and cold fluids, however, any flexible leak-resistant container having the proper temperature coefficient is acceptable. The flexible container 32 which encloses the fluid permits the stuffed toy 20 to be more fleshlike, resilient, and soft than other such toys. Further, the body weight of the stuffed toy 20 is nearly equivalent to that of the genuine animal due to the fluid within the container 32.

In order to insert the flexible fluid container 32 into the stuffed toy animal 20, the zipper means 34 is operated by way of example from the tail to the head portion opening the outer enclosure 22. The fluid container 32 may be filled with a hot fluid such as hot water for acting as a heat source or may be filled with cold water and ice cubes for acting as a heat sink. It is well known from the first law of thermodynamics, that heat flows from a higher temperature t1 to a lower temperature t2. Therefore, if the fluid container 32 is comprised of material which has an acceptable temperature gradient, then heat will radiate from the hot fluid across the interface of the container 32 and the outer enclosure 22 for several hours providing warmth to an individual or to a small pet while sleeping in cold weather.

Conversely, when the fluid container 32 houses cold fluid and ice cubes, heat will be drawn from the individual or small pet in warm weather providing a cooling effect. The stuffed toy animal 20 need only be in contact with the body of a human or a small pet in order to effect the desired heating and cooling effect. The effect may last for hours depending on how warm or cold the ambient air is. Since the stuffed toy animal 20 operates entirely without employing electrical heating circuits including batteries which often corrode resulting in damage to property and since the toy animal is completely fabricated from fire retardant material, the invention is completely safe for small children and pets.

Figure 7A:
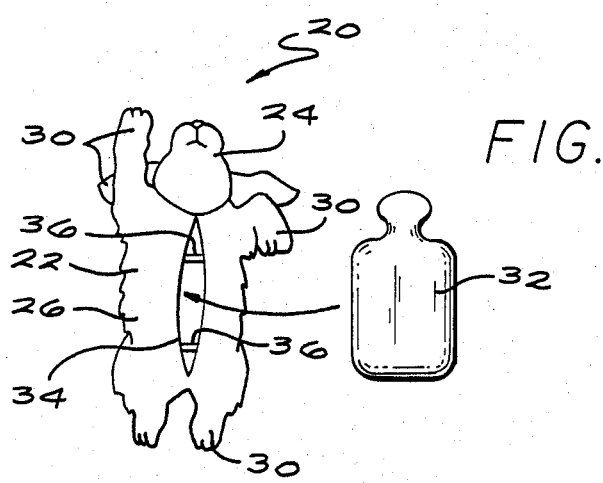
FIGS. 7A and 7B are planar views of the bottom portion of the stuffed toy animals shown in FIGS. 1A and 1B respectively illustrating the insertion of the fluid container.
Figure 7B:
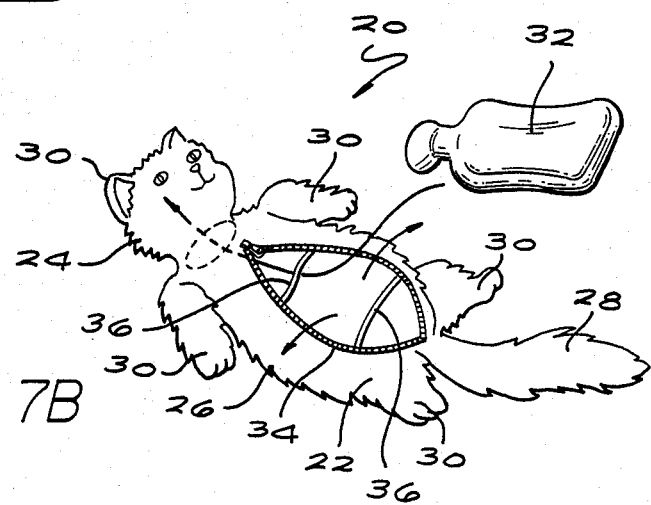

Once the container is filled with the desired fluid, the stopper is inserted. The stopper is designed to prevent leakage from the mouth of the fluid container 32 and includes a sealing means such as a rubber washer, grommet, or the like. Also, the stopper may include a threaded shaft for permitting the stopper to be threadedly screwed into the mouth of the fluid container. Once the stopper is inserted, the container is inserted into the body portion 26 through the open zipper means 34 and is positioned underneath the plurality of elastic straps 36 with the mouth of the container orientated towards the head portion 24 as is illustrated in FIGS. 7A and 7B. Once the container 32 is in position, the zipper means 34 is closed for example by operating the zipper handle from the head portion 24 to the tail 28. Once the container is in the proper position as is illustrated in FIGS. 5 and 6, the warming or cooling effect provided by the invention may be enjoyed.

Figure 8:
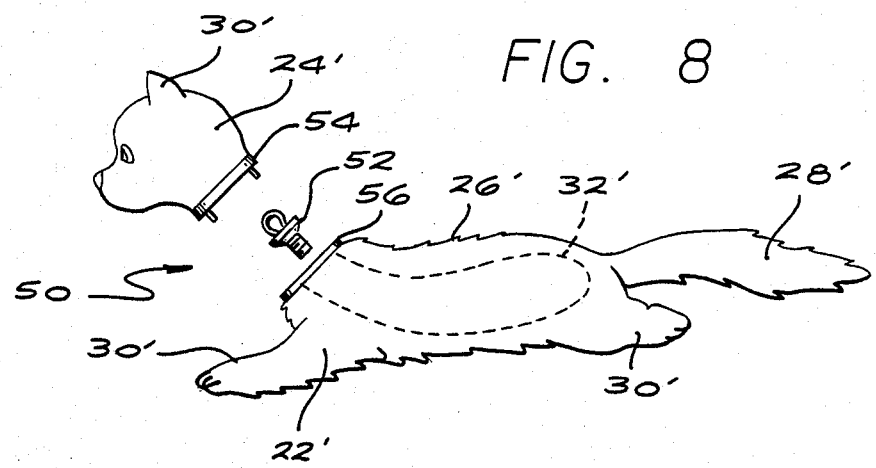
FIG. 8 is an exploded side elevational view of an alternative embodiment of a stuffed toy animal with an enclosed fluid container in accordance with the present invention.
Figure 9:
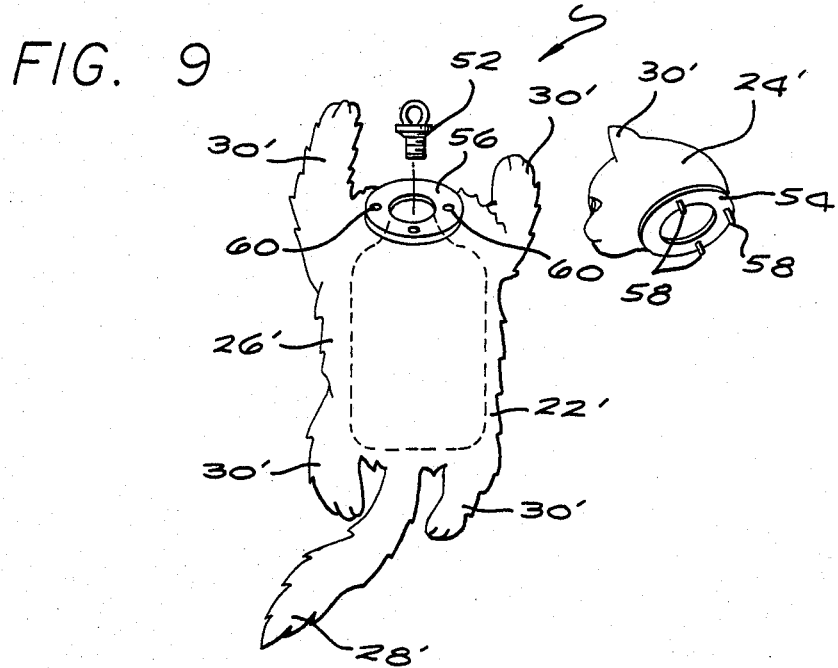
FIG. 9 is an exploded planar view of the back portion of the stuffed toy animal of FIG. 8 illustrating the fluid container in phantom, the head fitting ring and the collar base plate.
Figure 10:
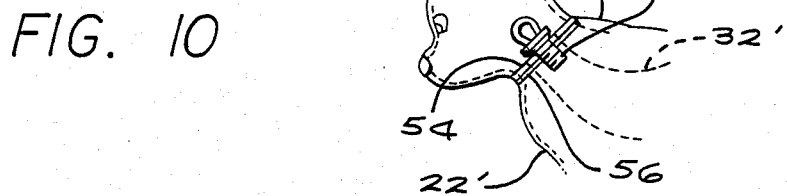
FIG. 10 is a side elevational view of the head portion of the stuffed toy animal of FIG. 8 illustrating the fluid container in phantom.

An alternative embodiment of the present invention is embodied in a stuffed toy animal with an enclosed fluid container and is referred to by the general reference numeral 50 and incorporates the present invention. In this instance, the alternative embodiment of the stuffed toy animal 50 is illustrated in FIGS. 8 through 10 and includes a structure similar to the stuffed toy animal 20 of the preferred embodiment (FIGS. 1 through 7B). Parts of the stuffed toy animal 50 of FIGS. 8 through 10 which find substantial correspondence in structure and function to those parts of FIGS. 1 through 7B, are designated with corresponding but primed reference numerals.

An exploded side elevational view of the stuffed toy animal 50 showing the flexible fluid container 32' is illustrated in FIG. 8. Additional elements of structure illustrated include a stopper 52 for sealing the container 32', a head fitting ring 54, a collar base plate 56 and a plurality of securing studs 58 extending from the head fitting ring 54. The plurality of securing studs 58 mate with a plurality of expandable receptacles 60 which are distributed about the collar base plate 56 and which are congruent with the securing studs.

The fluid container 32' is permanently installed within the body portion 26' as is illustrated in FIGS. 8 through 10. Since the container is permanently installed within the body portion, a zipper means providing access to the body portion is not necessary. Since the container 32' is "built-in" to the body portion 26' access to the container is provided by removing the head portion 24' as is illustrated in FIGS. 8 through 10. In the exploded views of FIGS. 8 and 9, the head portion 24' is shown removed from the body portion 26'. The head fitting ring 54 is connected to the base of the head portion 24' forming the neck of the stuffed toy animal 50. The head fitting ring, the collar base plate and associated structure is comprised of a flexible wear-resistant material such as, for example, plastic. The head fitting ring 54 is permanently connected to the base of the head portion 24' while the collar base plate 56 is permanently connected to the body portion 26' and also forms the mouth of the flexible container 32'. These permanent connections are made by any suitable manner known in the art such as by sewing, stapling or clamping to name a few.

The stopper 52 threadedly engages the mouth of the container 32' for providing leak resistance sealing and the plurality of securing studs 58 physically mesh with the corresponding expandable receptacles 60. Each securing stud 58 includes, for example, a flared plastic end which is somewhat larger in circumference than the corresponding expandable receptacle. The material flexibility coefficient of the plastic or like material which forms the securing studs and expandable receptacles permits sufficient compression and expansion of the plastic material to allow the stud to pass through the receptacle and act as a locking device without permanently damaging the plastic material. Sufficient force is required to separate the head portion 24' from the body portion 26' to expose the securing studs. This design prevents small children from removing the head of the stuffed toy animal 50 and harming themselves on the head fitting ring and associated securing studs.

The ring portion of the stopper 52 is seated above the collar base plate 56 and extends into the head portion 24'. By securing the head portion to the body portion of the stuffed toy animal 50 with the mounting scheme described, the ring portion of the stopper 52 is conveniently hid and non-accessible to small children. The head fitting ring 54 fits flush with the collar base plate 56 to provide a smooth continuous appearance in the furry surface of the outer enclosure 22' as illustrated in FIG. 10.

The remainder of the construction of the stuffed toy animal 50 is duplicate to that of the preferred embodiment 20 in that the material employed is fire-proof and of the quality and texture previously described. Since the container 32' is built into the stuffed toy animal 50, a plurality of elastic securing straps are not necessary to hold the container 32' in place.

An additional feature available in either the preferred embodiment 20 or the alternative embodiment 50 is the introduction of a noise generator. The noise generator is capable of creating audible sounds or even words for providing a perceived personality through the utterance of noises and words by the stuffed toy animal. The creation of words by the noise generator may be initiated, for example, by a pressure activated device located within the stuffed toy animal. The noise generator may be any of a plurality of commercially available noise or voice synthesizers which are capable of generating sounds, words, and even tunes of fairy tales.

From the foregoing, it will be appreciated that the stuffed toy animal of the present invention may be employed as a heat source or a heat sink for providing a heating or a cooling effect to a person or to a small pet. The flexible fluid container housed within the outer enclosure of the stuffed toy animal is capable of containing hot fluids as well as an ice and water combination for providing such heating and cooling effects. Further, the stuffed toy animal provides an efficient heat radiation and absorption device without requiring an electrical power supply, is fashioned from a non-flammable material, which is safe for use by children and is economical and inexpensive to manufacture. Additionally, in the preferred embodiment, the stuffed animal is convenient to disassemble for adding to or removing fluid from the flexible container and the outer enclosure is comprised of material which is washable for keeping the stuffed toy animal in a sanitary condition.

While two particular forms of the invention have been illustrated and described, it will also be apparent that various modifications can be made without departing from the spirit and scope of the invention. Accordingly, it is not intended that the invention be limited, except as by the appended claims.

What is claimed is:

1. A stuffed animal comprising, in combination:
   means for enclosing said stuffed animal having a head portion, a body portion and a plurality of extremities, said head portion being removable;
   means for containing a fluid, said containing means being permanently housed within said enclosing means and being comprised of flexible leakproof material for containing a fluid, said containing means adapted for transmitting and absorbing radiant energy, respectively, to and from said contained fluid;
   means for fastening said containing means to said enclosing means, said fastening means including a collar base plate in mechanical communication with said enclosing means and said containing means, said collar base plate having a center penetration for communicating with a interior of said containing means and for receiving a stopper for sealing said containing means; and
   means for fitting said head portion of said enclosing means to said fastening means for concealing said containing means, said fitting means including a fitting ring mounted to a base of said head portion, said fitting ring having a plurality of securing studs extending away from said head portion for mating with a plurality of expandable receptacles located in said collar base plate, said plurality of receptacles being congruent with said plurality of studs and said collar base plate mounted flush with said fitting ring.

2. The stuffed animal of claim 1 wherein said enclosing means comprises a fabric having a furry exterior.

3. The stuffed animal of claim 1 wherein said enclosing means comprises a fabric having a coarse knitted interior.

4. The stuffed animal of claim 1 wherein said fluid housed within said containing means is a hot fluid for transmitting radiant energy.

5. The stuffed animal of claim 1 wherein said fluid housed within said containing means is a cold fluid for absorbing radiant energy.

6. The stuffed animal of claim 1 wherein said plurality of expandable receptacles and said plurality of securing studs are comprised of plastic.

* * * * *